United States Patent [19]

Cziffer

[11] Patent Number: 5,464,414
[45] Date of Patent: Nov. 7, 1995

[54] DISPOSABLE APPROXIMATOR FOR APPROACHING NERVE-ENDINGS IN PARTICULAR FOR FACILITATING SEWING AND REPLACEMENT OF INJURED NERVES

[76] Inventor: Endre Cziffer, Bakats U. 5., II. 5, H-1093 Budapest, Hungary

[21] Appl. No.: 150,005

[22] PCT Filed: Nov. 5, 1992

[86] PCT No.: PCT/HU92/00046
§ 371 Date: Nov. 12, 1993
§ 102(e) Date: Nov. 12, 1993

[87] PCT Pub. No.: WO93/08727
PCT Pub. Date: May 13, 1993

[30] Foreign Application Priority Data

Nov. 6, 1991 [HU] Hungary ................... 3478/91

[51] Int. Cl.$^6$ .................................................. A61B 17/04
[52] U.S. Cl. .................................... 606/152; 606/150
[58] Field of Search ................... 606/155, 150–152

[56] References Cited

U.S. PATENT DOCUMENTS 4,617,702  10/1986  Diederich, Jr. ................ 24/17 AP
4,635,636  1/1987  Goldstein ....................... 606/150
4,723,548  2/1988  Lalonde ......................... 606/150

*Primary Examiner*—Gary Jackson
*Attorney, Agent, or Firm*—Ladas & Parry

[57] ABSTRACT

Disposable approximator for approaching nerve-endings particularly to facilitate sewing and replacement of injured nerves. The disposable approximator according to the invention comprises surgical metal hooks (3) known in the artwork. The approximator has a sliding leg (1) made of a synthetic material suitable for sanitary and surgical purposes. One surface thereof is designed with a structural formation allowing unidirectional displacement. At the end of the sliding leg (1) lying in direction of motion a fixed carrier-console (2) is arranged, into which one or more surgical metal hooks (3) are built-in that their ends are facing the direction of motion. Onto the sliding leg (1) a slide (4) is arranged, movable towards the fixed carrier-console (2), with a clearance enabling displacement. One or more surgical hooks (3) are built-in into the slide (4) so that their ends are facing the fixed carrier-console (2). In the inside of the slide (4) there is a structural formation allowing only unidirectional displacement of the slide (4) arranged on the sliding leg (1).

12 Claims, 3 Drawing Sheets

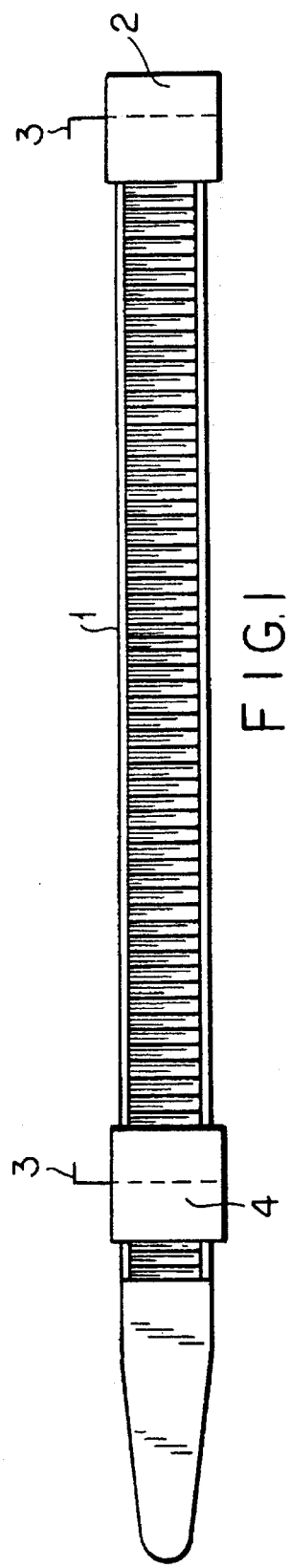
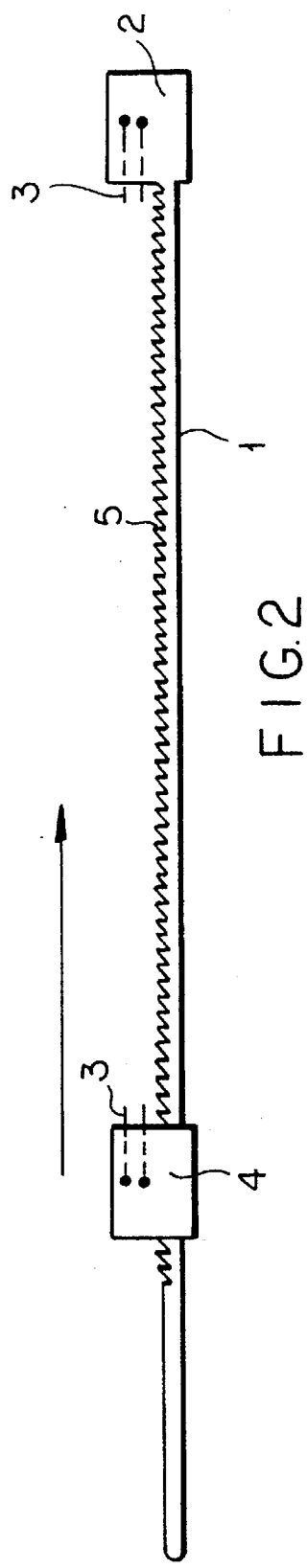

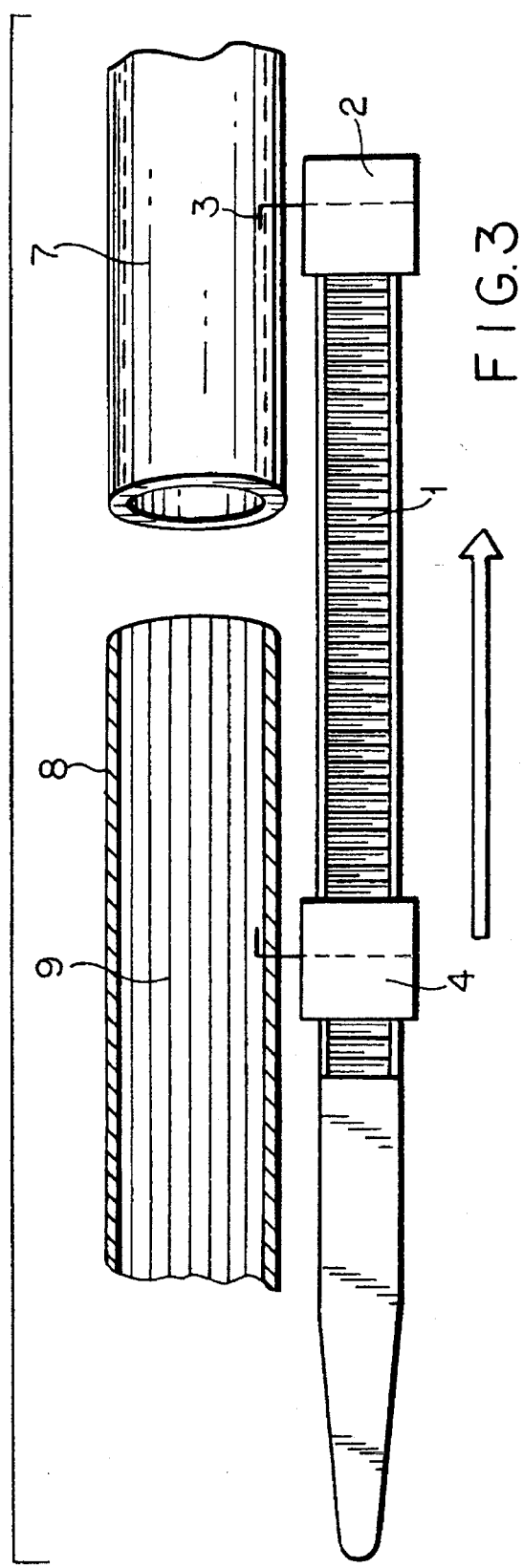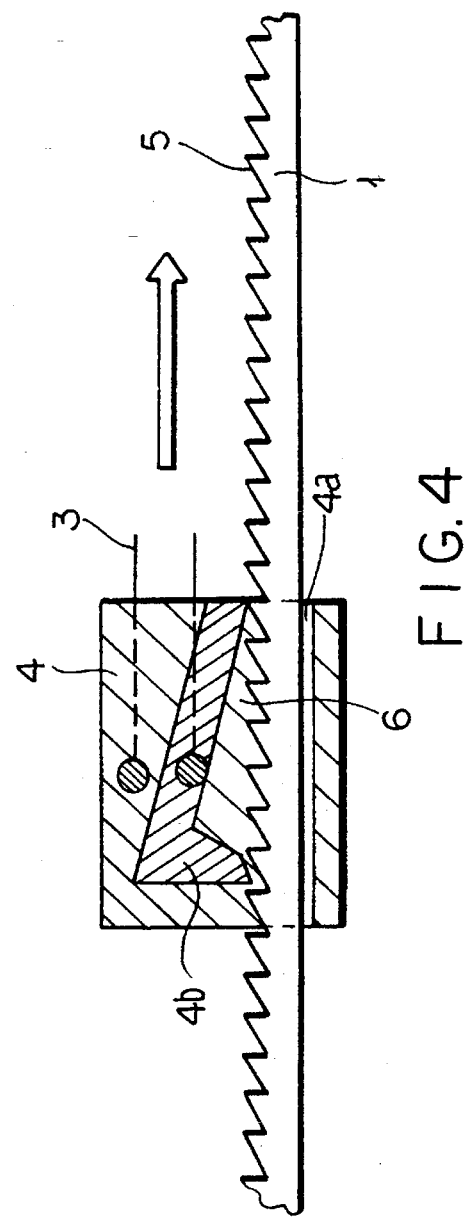

DISPOSABLE APPROXIMATOR FOR APPROACHING NERVE-ENDINGS IN PARTICULAR FOR FACILITATING SEWING AND REPLACEMENT OF INJURED NERVES

This is a continuation of application Ser. No. PCT/H692/00046, filed Nov. 5, 1992.

TECHNICAL FIELD

The invention relates to a disposable approximator for approaching nerve-endings, especially for facilitating suturing and replacement of injured nerves, containing metal surgical hooks which are known in the art.

BACKGROUND ART

The aim of surgeons has always been to treat injured nerves in a proper way, however, only in the last 20 years have surgical techniques, corresponding sewing materials, magnifying means needed for the accurate stitching of fine structures, and operating microscopes established suitable conditions. In the field of microsurgery pressing clips and different approximators for sewing micro-blood vessels already exist the force of pressure of which has been calibrated with utmost care. By means of said devices ends of blood vessels can be laid near to one another, so that sewing can be performed easily. As a consequence, there is no need to hold the ends of blood vessels by means of catgut of 20–30 microns, as this process may lead to the rupture of the catgut. The approximator is taking over the function for the full period of suturing. The approximator enables rotation of the blood vessel, accordingly concentric suturing becomes possible. With stitches of nerves, due to the fine thready structure of the nerves, there is no possibility to lay nerve-endings next to one another by means of clips arranged on the nerve-endings or by means of interconnecting slides.

Prior art devices tried to achieve approximation with thin needles passed through both nerve-endings transversally. By using this method we damaged thin, so called axial threads within the nerves i.e., fascicular structures. An alternative possibility is based on the recognition, that the envelope epineurium enclosing the nerve is relatively strong and by means of hooks hooked therein nerve-endings can be brought together without considerable damage. A device serving this purpose exists. It is a product of the German Company S&T. Said device consists of three components. It is made of metal. It is suitable for repeated use and it is most expensive. In case of multiple applications, fine surgical hooks may get damaged and subjected to deformation. Accordingly, when used repeatedly, it is dubious whether they can yield the advantages which can be achieved in the first application.

Due to an increase in diseases transferred with blood and bodily fluids (e.g. AIDS, Hepatitis etc.) use of disposable means seems to be more safe, and accordingly more advantageous. Moreover, problems appear in cleaning, sterilization, and packing of repeatedly used devices after use. In use further damage may occur in the structure of the microsurgical device, even when manipulated with utmost care. Repeated application of expensive instruments may become uncertain. For example, the device mentioned above marketed by the German Company S&T can be displaced on a smooth leg, however, there are no mechanical means provided which prevent sliding back.

SUMMARY OF THE INVENTION

The aim of the invention is to eliminate the drawbacks of approximators for approaching nerve-endings which have been developed up to now and to provide for a more inexpensive device which complies with biomechanical demands, which can be manipulated and applied easily, which is disposable and which can be mass, produced and used widely. A further requirement is to provide a simpler and quicker technique and to increase safety.

In basic conception, the invention is suitable for sanitary and surgical purposes, comprises elements made of metal and some synthetic material, and forms a complex unit. It does not contain independent elements. Accordingly, prior to use assembly becomes superfluous.

In accordance with the invention there is provided an approximator with a sliding leg made of some synthetic material suitable for hygiene and surgery. One surface of said sliding leg has a structural formation allowing unidirectional displacement. At the end of the sliding leg, facing the direction of motion, a fixed carrier console is arranged, into which one or more surgical metal hooks are built in. Ends of said hooks are oppositely arranged in respect to the direction of motion. On the sliding leg there is a slide which can be displaced towards the fixed carrier allowing connection with the structural formation and enabling unidirectional movement with a certain clearance. One or more surgical metal hooks are built into the slide, with their ends turned toward the fixed carrier console. In the inside of the slide, there is a structural formation connected with the structural formation on the sliding leg allowing unidirectional motion of the slide on the sliding leg.

Preferably the sliding leg has a flattened elliptic or cylindrical cross section. It is preferable for the sliding leg to be built together with the fixed carrier console.

The a structural formation allowing unidirectional displacement of the slide on the sliding leg comprises a toothing inclined in the direction of the carrier console, while in the inside of the slide there is an internal toothing, inclined opposite to the motion of direction of the slide. The latter toothing is provided with a profile fitting into the former toothing.

Surgical metal hooks arranged in the carrier console and/or in the slide preferabley have the shape of a rectangle, wherein one leg is perpendicular to the longitudinal axis of the sliding leg, while the other leg is parallel with its longitudinal axis.

The sliding leg and slide preferably are made of the same material. In application of the invention one group of the metal surgical hooks built into the fixed carrier console is hooked into the outer epineurium of one of the nerve-endings, while the metal surgical hooks belonging to the other group built into the unidirectionally moving slide are engaged with the epineurium of another nerve-end. Since the ends of the surgical metal hooks of the respective groups are facing each other, by moving the slide toward the fixed carrier console a unidirectional approach of the respective nerve-endings can be achieved. Moreover, in an ideal case, they can be laid next to each other. If complete approach cannot be obtained because some material is missing in the nerve, replacement of the nerve missing can be realized by nerve-graft, in the same manner as without using an approximator. As already mentioned, the sliding leg and slide have been designed so that only displacement in direction of the carrier console is allowed and, sliding back will be prevented.

Preparation of nerve stitching will be facilitated by means of the free long part of the sliding leg. The nerve can be put remotely into a circular motion and sutured concentrically without hindering the hand performing operation. After stitching, the device according to the invention will be removed so that, between the carrier console and the slide, the sliding leg is cut through with scissors, and metal hooks are released from the nerve-endings. In such a manner repeated use of the device will be rendered impossible. Once the surgical hooks are disengaged from the nerve, repeated use must not occur. Since the structural design of the construction allows unidirectional motion, return to the starting position becomes impossible.

The disposable approximator according to the invention is designed for non-recurrent use, since disassembly after application makes repeated use impossible. Toothing in the sliding leg and in the slide prevent unexpected sliding apart of the device. Accordingly suturing of nerves can be performed with maximal safety.

BRIEF DESCRIPTION OF DRAWINGS

The invention will be detailed by the way of an exemplary embodiment and with reference to the enclosed drawings wherein FIG. 1 is a plan view of the disposable nerve approximator according to the invention; FIG. 2 is a side-view of the disposable approximator according to FIG. 1

FIG. 3 shows a schematic side-view of the approximator during its use;

FIG. 4 is a longitudinal sectional view of a part of the sliding leg and of the slide.

BEST MODE OF CARRYING OUT THE INVENTION

Figure 5:
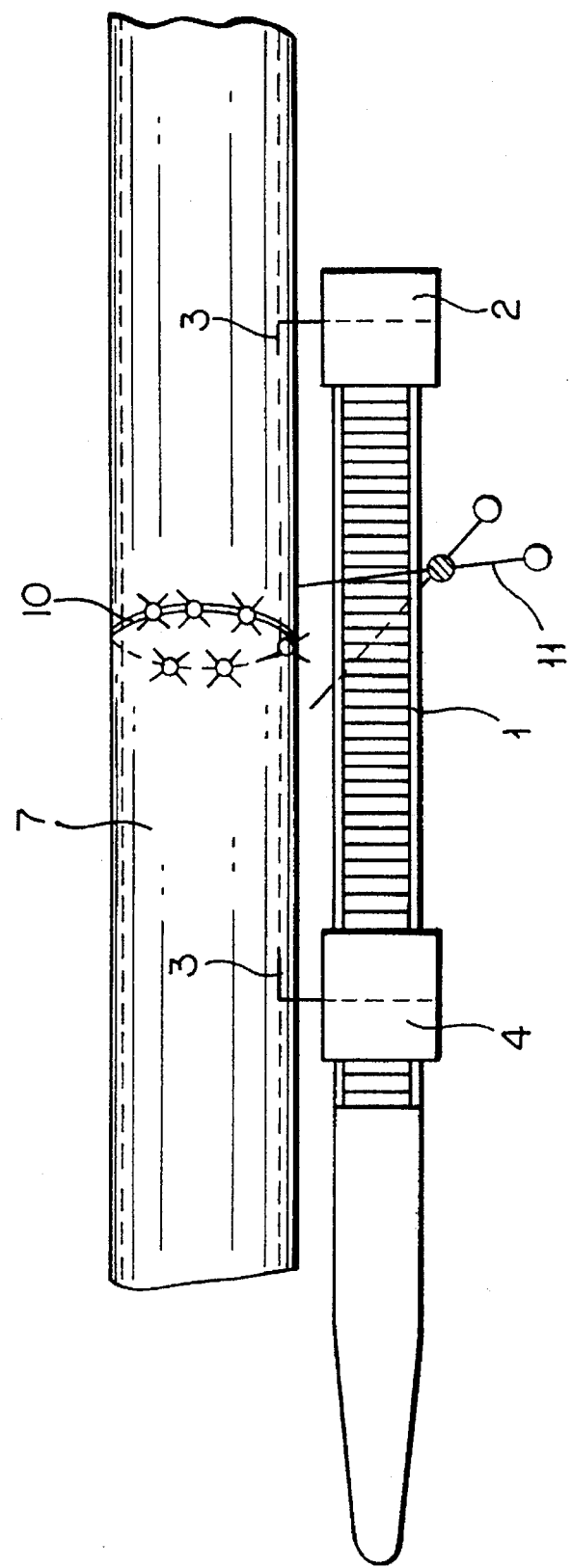
FIG. 5 illustrates one phase of removal of the device after having finished suturing.

As can be seen in FIGS. 1 and 2 the device for non-recurrent use - the disposable approximator - consists of a flattened sliding leg 1, at the end of which a monolithic fixed carrier-console 2 is arranged. On the sliding leg 1, along nearly its full length, a toothing 5 is formed which is inclined towards the fixed carrier-console 2.

In the fixed carrier-console 2, metal hooks 3 - known in the art - which are suitable for sanitary and surgical purposes are built-in at a predetermined distance from each other, facing the sliding-leg 1. In proximity of the other end of the sliding leg 1 a slide 4 containing a through-hole 4a and a pawl 4b (see FIG. 4) is arranged. As a practical matter, dimensions of the slide 4 correspond with the dimensions of the fixed carrier-console 2. In the slide 4 one or more metal hooks 3 are built-in at a predetermined mutual distance, with the ends of the hooks facing the fixed carrier-console 2. Internal toothing 6 is formed in the slide 4. Toothing 6 is inclined in an opposite direction in respect to toothing 5 of the sliding-leg 1, and has a negative complementary shape with respect thereto. In such manner, after having engaged toothing 5 and 6, slide 4 can be displaced in one direction only, namely towards the fixed carrier-console 2. Clearance between the sliding leg 1 and the slide 4 allows displacement of the slide 4 with an inconsiderable force, in course of which teeth of toothings 5 and 6 leap over one another, thus enabling displacement of the slide 4. Due to the inclination of the respective teeth 5 and 6 in opposite direction, the slide 4 cannot be displaced in an opposite direction.

After having pushed slide 4 onto the first teeth of the toothing 5 of the sliding leg 1, the device will be a monolithic unit and can be disassembled in this condition. Preferably surgical hooks 3 have a rectangular shape, whereas one leg is perpendicular to the longitudinal axis of the sliding leg 1, while the other runs parallel therewith. Depth-size of surgical hooks 3 considers thickness of the external epineurium 8 of the nerve 7, thus preventing deep penetration, avoiding destruction of axial threads 9.

After stitching, the sliding leg 1 will be cut with scissors between the fixed carrier-console 2 and slide 4. Thereafter disengagement and removal of the metal hooks 3 can be performed easily. By using the nerve approximator, designed for non-recurrent use, fixation of injured nerves and approach of nerve-endings can be performed without additional damage to the nerves.

Metal hooks can be hooked into the nerve further from the place of injury. Accordingly, the hooks are not in the proximity of the stitch and thus the device does not hinder preparation of the stitches.

The disposable approximator according to the invention can be applied quickly, use thereof is simplified and considerable practice is not required. For any surgeon skilled in nerve surgery there will be no technical difficulties. By means of the approximator any concentric stitch can be easily prepared with both nerve-endings corotating. Duration of operations can be considerably shortened, as a result, and expensive sewing material (catgut) can be saved since frequent rupture can be avoided.

The disposable approximator according to the invention is designed for non-recurrent use. It can be thrown away, and further expenditure (on cleaning, soaking material for blood dissolution, sterilization, packing) become superfluous.

By using the disposable approximator according to the invention safety of the stitch can be increased, and later results can be improved. Resultant techniques assure accurate performance of operation. Due to its cheapness, the approximator of the invention can be considered as a consumable supply in the field of therapeutics. It can be packed in uniform sterile sets and can be sterilized by using known sterilizing methods (gas, gamma radiation heated air.)

After placement of the disposable approximator onto the injured nerve, it can not be disassembled only after destruction. In course of application it does not disturb the surgeon in stitching. Its space requirement is minimal.

I claim:

1. An approximator for facilitating suturing of nerve endings comprising:

an elongated leg member having proximal and distal portions and provided with a slide and a carrier console thereon, said slide being slidably disposed on the leg so that it is slidably displaceable along the leg member in only one direction from said distal portion on the leg to said proximal portion closer toward the proximal portion with the carrier console, said slide and said carrier console each being provided with at least one surgical hook therein for hooking onto nerve endings such that a first nerve ending hooked by the hook at least one of the slide is brought into proximity with a second nerve ending hooked by the at least one hook of the carrier console when the slide is displaced from said distal position to said proximal position whereby to facilitate suturing of the first and second nerve endings.

2. An approximator as claimed in claim 1 wherein the leg (1) has a cross-section selected from the group consisting of flattened, elliptic or cylindrical cross-section.

3. An approximator as claimed in claim 1 wherein the leg (1) and the carrier-console (2) are formed as a monolithic unit.

4. An approximator as claimed in claim 1 comprising a leg toothing (5) on the leg (1) with an inclination towards the carrier-console (2), the slide (4) comprising an internal toothing (6) with a profile fitting into the leg toothing (5) and inclined opposite to the direction of displacement of the slide (4).

5. An approximator as claimed in claim 1, wherein the leg comprises inclined teeth and the slide comprises internal teeth which engage the inclined teeth to permit displacement only in said one direction.

6. An approximator as claimed in claim 5, wherein said leg member further comprising pawl means on a surface thereof for preventing the slide from moving in a direction away from the carrier console.

7. An approximator as claimed in claim 5, wherein the at least one hook of the slide have ends which face the carrier console.

8. An approximator as claimed in claim 7, wherein the at least one hook of the carrier console have ends which face the slide.

9. An approximator as claimed in claim 8, wherein the carrier console is fixed to the leg.

10. An approximator as claimed in claim 9, wherein the at least one hook of the slide and the hook or hooks of the carrier console are metal.

11. An approximator as claimed in claim 10 wherein the metal hooks (3) of both the carrier console and the Slide have a rectangular shape, each metal hook having a first portion and a second portion with the first portion being perpendicular to the longitudinal axis of the leg (1) and the second portion being parallel with the longitudinal axis of the leg.

12. An approximator as claimed in claim 11 wherein the slide (4) and leg (1) are made of the same material.

* * * * *